(12) United States Patent
Kim et al.

(10) Patent No.: US 8,928,234 B2
(45) Date of Patent: Jan. 6, 2015

(54) LIGHTING APPARATUS (75) Inventors: Ji Young Kim, Seoul (KR); Eun Seok Choi, Seoul (KR); Ji Hye Hwang, Seoul (KR); Mi Sun Hwang, Seoul (KR); Hae Rim Park, Seoul (KR); Min Su Park, Seoul (KR)

(73) Assignee: LG Electronics Inc., Seoul (KR)

( * ) Notice: Subject to any disclaimer, the term of this patent is extended or adjusted under 35 U.S.C. 154(b) by 467 days.

(21) Appl. No.: 12/966,119

(22) Filed: Dec. 13, 2010

(65) Prior Publication Data

US 2011/0138905 A1 Jun. 16, 2011

(30) Foreign Application Priority Data

Dec. 14, 2009 (KR) ........................ 10-2009-0123672

(51) Int. Cl.
  *H05B 37/00* (2006.01)
  *G01F 23/296* (2006.01)
  *F21V 33/00* (2006.01)
  *G01K 13/00* (2006.01)
  *A61L 2/10* (2006.01)
  *F21Y 101/02* (2006.01)
  *F21Y 113/00* (2006.01)

(52) U.S. Cl.
  CPC ............ *G01F 23/2962* (2013.01); *F21V 33/00* (2013.01); *G01K 13/00* (2013.01); *A61L 2/10* (2013.01); *F21Y 2101/02* (2013.01); *F21Y 2113/005* (2013.01); *Y10S 362/806* (2013.01)
  USPC ............................. 315/193; 362/154; 362/806

(58) Field of Classification Search
  USPC ....... 315/129, 133, 136, 193, 185 S; 362/605, 362/632, 559, 565, 154, 362, 806, 362/311.01–311.15, 171, 178, 157, 231, 362/640, 364, 249.02; 73/290 R; 374/150, 374/E13.001, E13.012
  See application file for complete search history.

(56) References Cited

U.S. PATENT DOCUMENTS

| | | | | |
|---|---|---|---|---|
| 5,770,153 A | * | 6/1998 | Wagner | 422/79 |
| 6,180,003 B1 | * | 1/2001 | Reber et al. | 210/198.1 |
| 6,382,416 B1 | * | 5/2002 | Gainey | 206/317 |
| 7,202,484 B1 | * | 4/2007 | Tantillo | 250/455.11 |
| 7,318,656 B1 | * | 1/2008 | Merine | 362/154 |
| 2004/0182929 A1 | * | 9/2004 | Aoshima et al. | 235/454 |
| 2005/0056663 A1 | * | 3/2005 | Yu | 222/113 |
| 2005/0236998 A1 | * | 10/2005 | Mueller et al. | 315/51 |
| 2006/0152946 A1 | * | 7/2006 | Chien | 362/641 |

(Continued)

FOREIGN PATENT DOCUMENTS

| | | | | |
|---|---|---|---|---|
| DE | 19909577 A1 | * | 9/2000 | G01D 7/12 |
| JP | 3144910 | | 9/2008 | |

(Continued)

OTHER PUBLICATIONS

Korean Notice of Allowance issued in related Application No. 10-2009-0123672 dated Feb. 21, 2014.

*Primary Examiner* — Tuyet Thi Vo
*Assistant Examiner* — Henry Luong
(74) *Attorney, Agent, or Firm* — Ked & Associates, LLP (57) ABSTRACT

A lighting apparatus is disclosed. The lighting apparatus is capable of achieving improved aesthetics by irradiating mood lighting into a storage container and also, of functioning to display a variety of status information about the storage container to the outside and to sterilize the interior of the storage container.

16 Claims, 10 Drawing Sheets

(56) References Cited

U.S. PATENT DOCUMENTS

2007/0261487 A1* 11/2007 Sintes et al. .................. 73/290 V
2008/0122376 A1*  5/2008 Lys ............................... 315/192
2010/0254135 A1* 10/2010 Bayat et al. ................... 362/235
2011/0038754 A1*  2/2011 James ............................ 422/24

FOREIGN PATENT DOCUMENTS

| KR | 10-1988-0000580 | | 4/1988 | | |
| KR | 10-0572335 | | 4/2006 | | |
| KR | 10-2010-0077651 | | 7/2010 | | |
| KR | 20100077651 A | * | 7/2010 | ............. | B65D 51/24 |

* cited by examiner

LIGHTING APPARATUS

This application claims the benefit of Korean Patent Application No. 10-2009-0123672, filed on Dec. 14, 2009, which is hereby incorporated by reference as if fully set forth herein.

BACKGROUND OF THE INVENTION

1. Field of the Invention

The present invention relates to a lighting apparatus, and more particularly, to a lighting apparatus which can achieve improved aesthetics by irradiating mood lighting into a storage container and also, can function to display a variety of status information about the storage container to the outside and to sterilize the interior of the storage container.

2. Discussion of the Related Art

Lighting has played a key role in advance in human culture and has been closely connected to the advancement of the human race since the dawn of time.

Recently, advances in the lighting industry have progressed at a vigorous pace and numerous studies related to light sources, light emitting methods, driving methods and efficiency enhancement have been conducted.

Examples of current light sources used in lighting apparatuses include incandescent bulbs, fluorescent lamps and discharge lamps. These light sources have been used for a variety of purposes, such as domestic, industrial, and outdoor purposes.

However, light sources operating based upon electrical resistance, such as incandescent bulbs, etc., have problems of low efficiency and high heat loss, discharge lamps are expensive and exhibit poor energy efficiency, and fluorescent lamps have a problem of environment pollution due to use of mercury.

To solve disadvantages of these light sources, interest in light emitting diodes, which have a great number of advantages, such as high efficiency and realization of various colors and designs, etc., is increasing.

In particular, demand for a surface light source having more uniform optical characteristics than point/linear light sources is increasing.

SUMMARY OF THE INVENTION

Accordingly, the present invention is directed to a lighting apparatus that substantially obviates one or more problems due to limitations and disadvantages of the related art.

An object of the present invention is to provide a lighting apparatus which can achieve improved aesthetics by irradiating mood lighting into a storage container and also, can function to display a variety of status information about the storage container to the outside and to sterilize the interior of the storage container.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, a lighting apparatus includes a main body, a light-emitting unit including a substrate placed in the housing and at least one Light Emitting Diode (LED) mounted on the substrate, an electronic module to apply power to the light-emitting unit, a switch to connect the light-emitting unit and the electronic module to each other, and a controller to control operation of the light-emitting unit.

In accordance with another aspect of the present invention, a lighting apparatus includes a storage container having an opening, and a cover member including a main body to selectively open or close the opening of the storage container, a light-emitting unit provided in the main body to irradiate light into the storage container, an electronic module to apply power to the light-emitting unit, a switch to connect the light-emitting unit and the electronic module to each other, and a controller to control operation of the light-emitting unit.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Reference will now be made in detail to the preferred embodiments of the present invention, examples of which are illustrated in the accompanying drawings. The accompanying drawings illustrate exemplary embodiments of the present invention and provide a more detailed description of the present invention. However, the scope of the present invention should not be limited thereto.

In accordance with one aspect of the present invention, there is provided a lighting apparatus including a main body, a light-emitting unit including a substrate placed in the housing and at least one Light Emitting Diode (LED) mounted on the substrate, an electronic module to apply power to the light-emitting unit, a switch to connect the light-emitting unit and the electronic module to each other, and a controller to control operation of the light-emitting unit.

In accordance with another aspect of the present invention, there is provided a lighting apparatus including a storage container having an opening, and a cover member including a main body to selectively open or close the opening of the storage container, a light-emitting unit provided in the main body to irradiate light into the storage container, an electronic module to apply power to the light-emitting unit, a switch to connect the light-emitting unit and the electronic module to each other, and a controller to control operation of the light-emitting unit.

Here, the cover member constituting the lighting apparatus according to the secondly described aspect of the present invention may be understood to have the same meaning as the lighting apparatus according to the firstly described aspect of the present invention.

Figure 1:
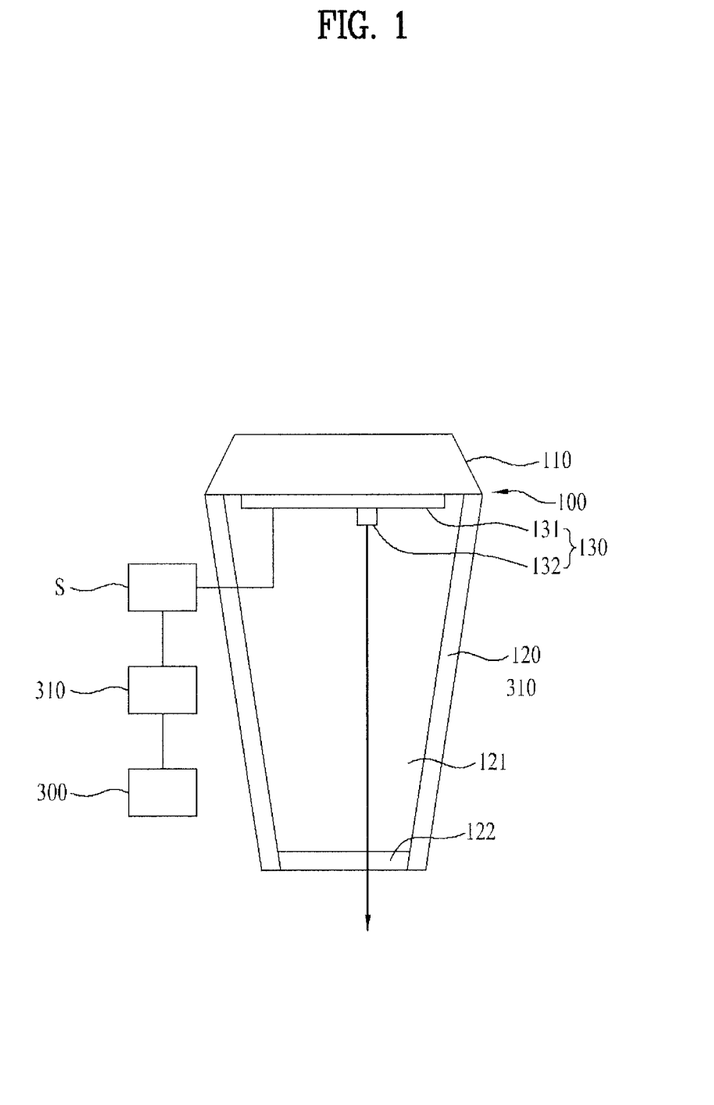
FIG. 1 is a schematic sectional view illustrating a lighting apparatus according to an embodiment of the present invention.
Figure 2:
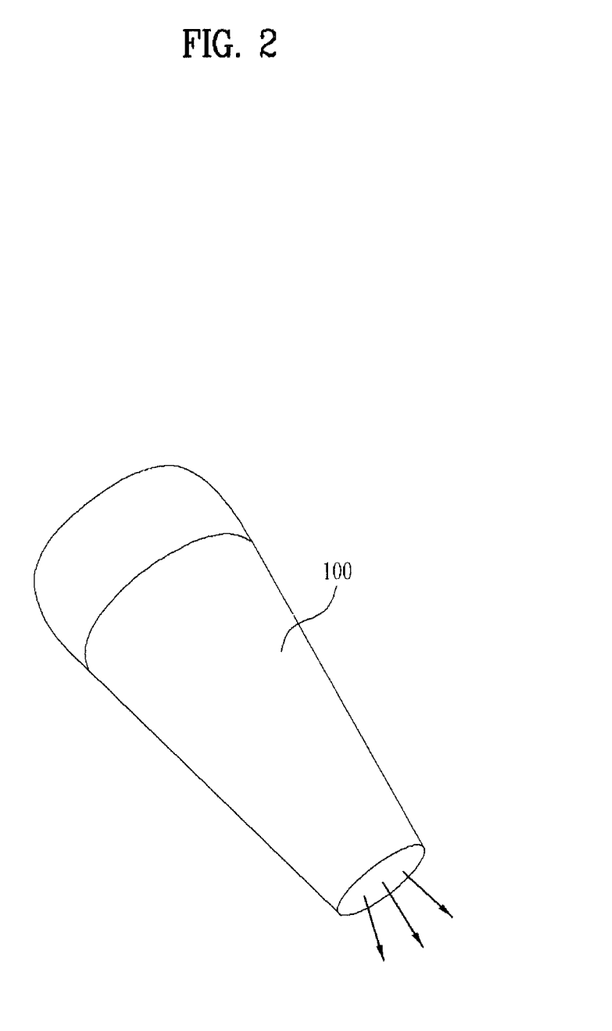
FIG. 2 is a perspective view of the lighting apparatus according to the embodiment of the present invention.

FIG. 1 is a schematic sectional view illustrating a lighting apparatus according to an embodiment of the present invention, and FIG. 2 is a perspective view of the lighting apparatus according to the embodiment of the present invention.

The lighting apparatus 100 according to the embodiment of the present invention includes a main body, a light-emitting unit 130 including a substrate 131 placed inside the main body and at least one light-emitting diode 132 mounted on the substrate 131, an electronic module 310 to apply power to the light-emitting unit 130, a switch S to connect the light-emitting unit 130 and the electronic module 310 to each other, and a controller 300 to control operation of the light-emitting unit 130.

The main body may include a first body 120 having a light guide hole 121, both longitudinal ends of which are open, a second body 110 provided at one longitudinal end of the first body 120, and a transparent window 122 placed inside the light guide hole 121.

The second body 110 may be attached to the longitudinal end of the first body 120 by an adhesive, thereby serving to close one open longitudinal end of the light guide hole 121.

The light-emitting unit 130 may be mounted to the second body 110 such that the light-emitting diode 132 irradiates light toward the transparent window 122.

With the above-described configuration, if the electronic module 310 applies power to the light-emitting unit 130, the light-emitting diode 132 irradiates light. The irradiated light is directed through the light guide hole 121, thereby being discharged to the outside through the transparent window 122.

The first body 120 may be made of rubber or an elastic resin so as to be inserted into a bottle or a container (hereinafter referred to as a storage container).

The light-emitting diode 132 may function to irradiate Ultra Violet-C (UVC) light.

The switch S may function to turn on or off the lighting apparatus 100 and may be provided at one side of the second body 110.

In the case where the second body 110 is mounted to the first body 120 in a rotatable manner, the lighting apparatus 100 may be turned on or off via rotation of the second body 110.

Referring to FIG. 1, the lighting apparatus 100 according to the embodiment of the present invention may take the form of a cap of a storage container 200 and thus, the first body 120 of the main body may be inserted into the storage container 200.

To ensure that the lighting apparatus 100 can be easily inserted into an opening of the storage container 200 to achieve an effective seal upon complete insertion, the first body 120 is preferably made of an elastic material, such as rubber.

The lighting apparatus 100 according to the embodiment of the present invention may further perform a sterilizing function (hereinafter referred to as a sterilization mode) on contents 210 stored in the storage container 200 by irradiating UVC light from the UVC light-emitting diode 132.

UVC is the highest energy band of the UV spectrum and, as such, is referred to as "sterilizing light". UVC may perform a sterilizing function by denaturing the DNA and RNA of microorganisms, such as bacteria, viruses, mold and the like, and generating ozone.

Accordingly, the lighting apparatus 100 according to the embodiment of the present can sterilize the contents 210 of the storage container 200 by use of the UVC light-emitting diode 132 mounted to a cap or a cover member of the storage container 200.

Figure 3:
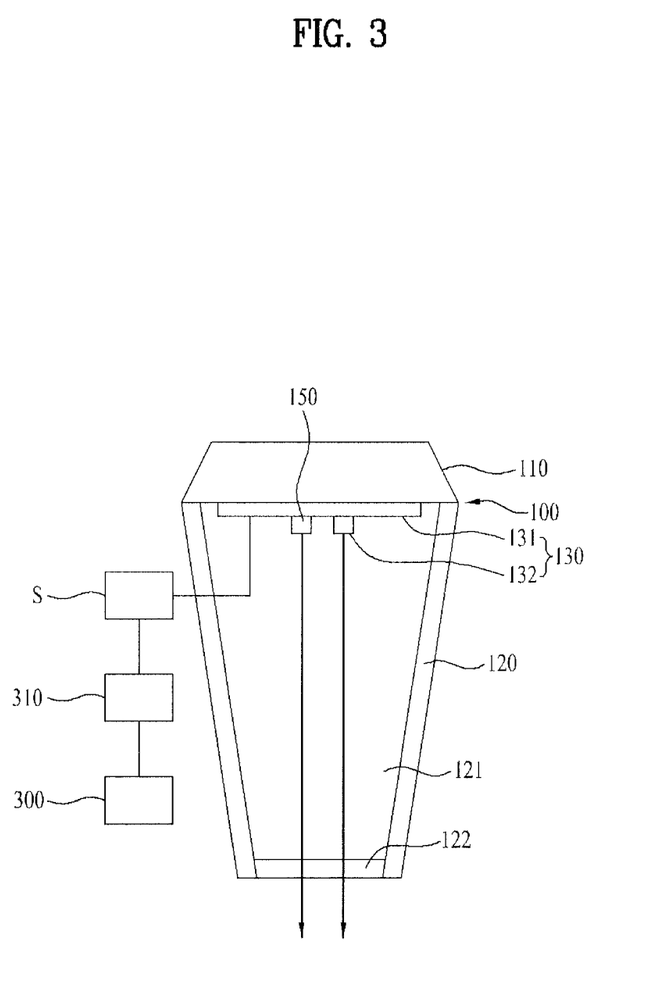
FIG. 3 is a schematic sectional view illustrating a lighting apparatus according to a first embodiment of the present invention.

FIG. 3 is a schematic sectional view illustrating a lighting apparatus according to a first embodiment of the present invention.

The lighting apparatus 100 according to the first embodiment of the present invention may include a light-emitting diode 150 to irradiate mood lighting into the storage container 200.

Specifically, the light-emitting unit 130 may further include an ornamental light-emitting diode 150 functioning to emit mood lighting towards the transparent window 122.

For example, if the mood lighting is irradiated (hereinafter referred to as a mood lighting mode), the irradiated light may exhibit gradual progression in the interior of the storage container 200.

To this end, the ornamental light-emitting diode 150 may be a package containing at least one selected from among a red light-emitting diode chip, a green light-emitting diode chip and a blue light-emitting diode chip and may be mounted on the substrate 131.

For example, the ornamental light-emitting diode 150 may be a module in which a red light-emitting diode chip, a green light-emitting diode chip and a blue light-emitting diode chip constitute a single package, or may be a module in which a red light-emitting diode package, a green light-emitting diode package and a blue light-emitting diode package are mounted respectively on a printed circuit board.

Figure 4:
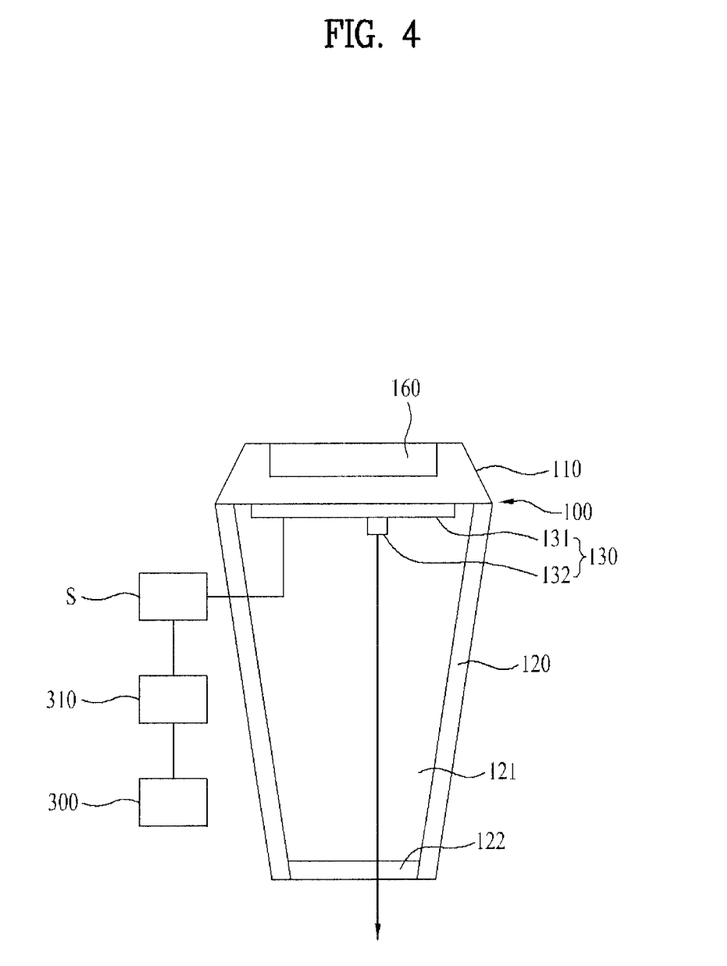
FIG. 4 is a schematic sectional view illustrating a lighting apparatus according to a second embodiment of the present invention.

FIG. 4 is a schematic sectional view illustrating a lighting apparatus according to a second embodiment of the present invention.

Referring to FIGS. 1 and 4, the controller 300 may include an input unit (not shown) to input a control command including an operating mode and a display unit 160 provided at the main body and serving to output a variety of status information to the outside.

In the lighting apparatus 100 according to the present embodiment, the display unit 160 may be provided in the second body 110 and may take the form of a touch screen. In this case, the input unit (not shown) may be provided on the touch screen.

The operating mode may include a sterilization mode or a mode lighting mode as described above. In this case, the light-emitting unit 130 may include the UVC light-emitting diode 132 to irradiate UVC light and the ornamental light-emitting diode 150 to irradiate mood lighting.

A user may select whether to perform a sterilization mode or a mood lighting mode by use of the display unit (160, for example, a touch screen) provided in the second body 110 of the main body that is exposed from the storage container 200.

If the operating mode selected by the user is input, the controller 300 generates a control signal related to the corresponding operating mode and the electronic module 310 may operate the light-emitting unit 130 based on the control signal.

The display unit 160 is exposed from the storage container 200 and may display a variety of information related to the status of the storage container 200.

Figure 5:
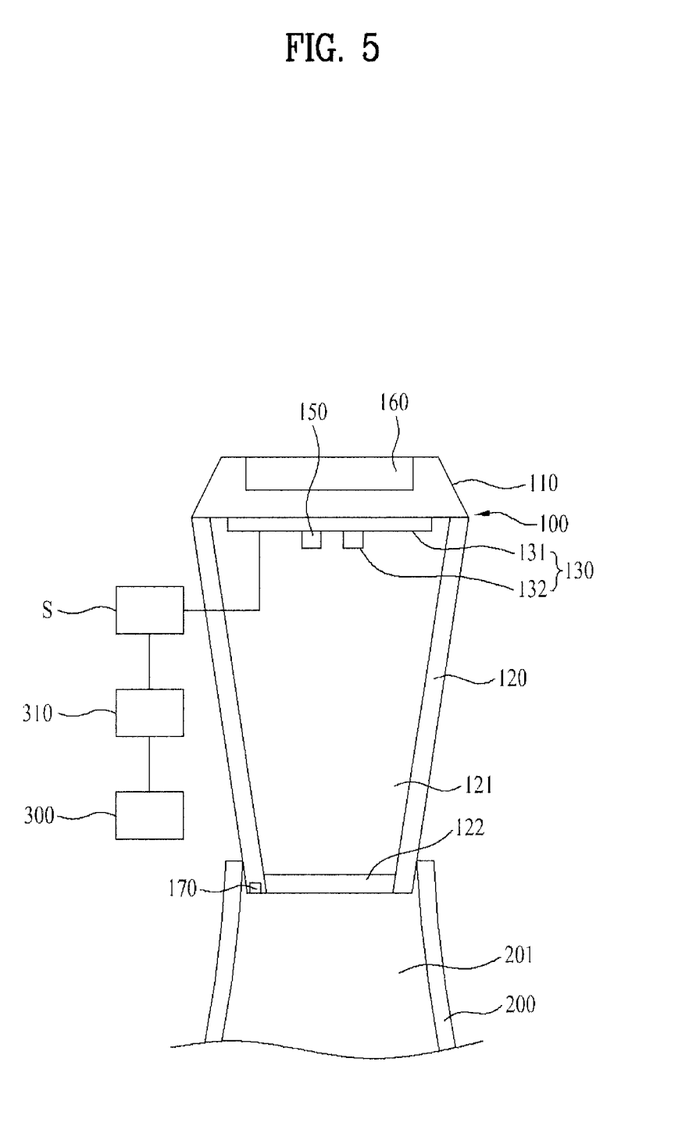
FIG. 5 is a schematic sectional view illustrating a lighting apparatus according to a third embodiment of the present invention.

FIG. 5 is a schematic sectional view illustrating a lighting apparatus according to a third embodiment of the present invention.

The status information may contain an interior temperature of the storage container 200, and the lighting apparatus 100 may include a temperature sensor 170 to sense the interior temperature of the storage container 200.

That is, in the lighting apparatus 100 according to the third embodiment, the temperature sensor 170 may be placed in the lighting apparatus 100 and serves to sense a temperature of an interior space 201 of the storage container 200.

In an embodiment, the temperature sensor 170 may be positioned on an inner surface of one longitudinal end of the first body 120 in a state in which the second body 120 is attached to the other longitudinal end of the first body 120.

Figure 6:
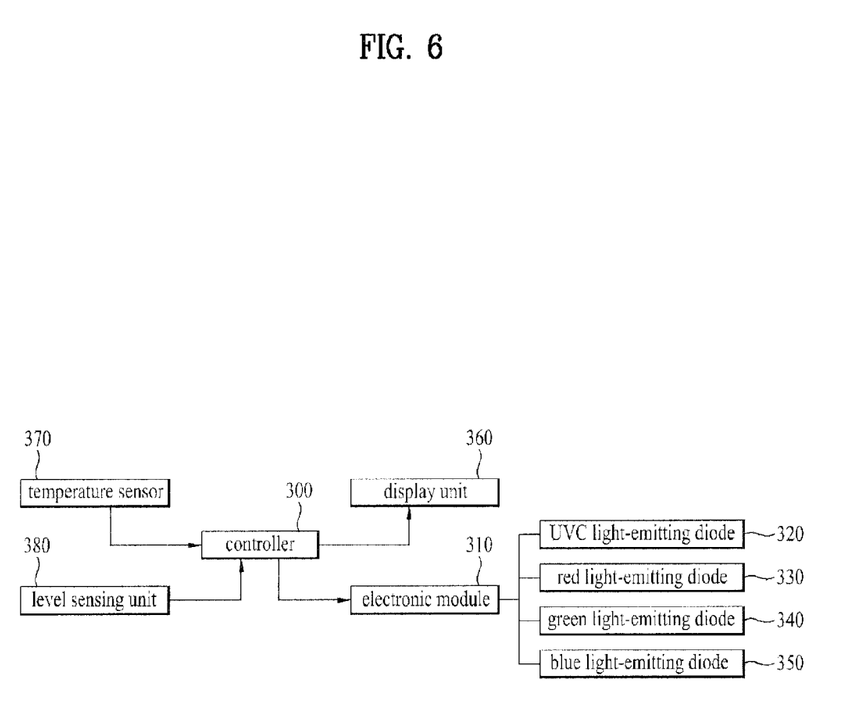
FIG. 6 is a schematic block diagram of the lighting apparatus according to the present invention.

FIG. 6 is a schematic block diagram of the lighting apparatus according to the present invention.

As described above, the lighting apparatus may include a light-emitting diode module, which can emit mood lighting and consists of a red light-emitting diode 330, a green light-emitting diode 340, a blue light-emitting diode 350 and the UVC light-emitting diode 320, an electronic module 310 to apply power to the light-emitting diode module, a temperature sensor 370 to sense the interior temperature of the storage container, and a display unit 360 to display a variety of status information.

The lighting apparatus may further include a level sensing unit 380 to sense the level of contents received in the storage container.

In addition, the electronic module 310, the display unit 360, the temperature sensor 370 and the level sensing unit 380 may be controlled by the controller 300.

With this configuration, if the controller 300 outputs a control signal to the electronic module 310, the red light-emitting diode 330, the green light-emitting diode 340, the blue light-emitting diode 350 and the UVC light-emitting diode 320 are selectively operated, enabling implementation of a sterilization mode or a mood lighting mode.

In addition, the controller 300 may selectively operate the display unit 360, the temperature sensor 370 and the level sensing unit 380 to ensure that the display unit 360 can display a variety of status information in the form of images and the like, the temperature sensor 370 can sense the interior temperature of the storage container and the level sensing unit 380 can sense the level of contents received in the storage container.

In an embodiment, if the user selects various operating modes required to selectively operate the display unit 360, the temperature sensor 370, the level sensing unit 380, the red light-emitting diode 330, the green light-emitting diode 340, the blue light-emitting diode 350 and the UVC light-emitting diode 320 by use of the input unit (not shown), the controller 300 outputs a control signal to one of the display unit 360, the temperature sensor 370, the level sensing unit 380 and the electronic module 310 upon receiving an input signal output from the input unit.

For example, if the user selects a sterilization mode, the controller 300 outputs a control signal to the electronic module 310. The electronic module 310 operates the UVC light-emitting diode 320 in response to the control signal, allowing UVC light to be irradiated to the contents received in the storage container. In this way, sterilization of the contents may be performed.

The display unit 360 may function to display the interior temperature of the storage container sensed by the temperature sensor 370, or may function to display the level of contents received in the storage container sensed by the level sensing unit 380.

Of course, the display unit 360 may display the sterilization mode.

Figure 8:
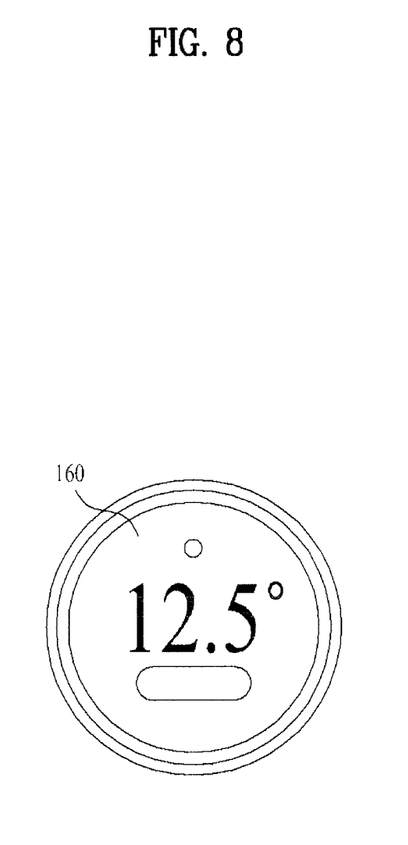
FIG. 8 is a plan view illustrating a display unit provided in a lighting apparatus according to the present invention.

Specifically, referring to FIG. 8, the controller may control the display unit 160 so as to display a text image "12.5" that represents the interior temperature of the storage container and a text image "Sterilize" that represents the current operating mode.

Figure 7:
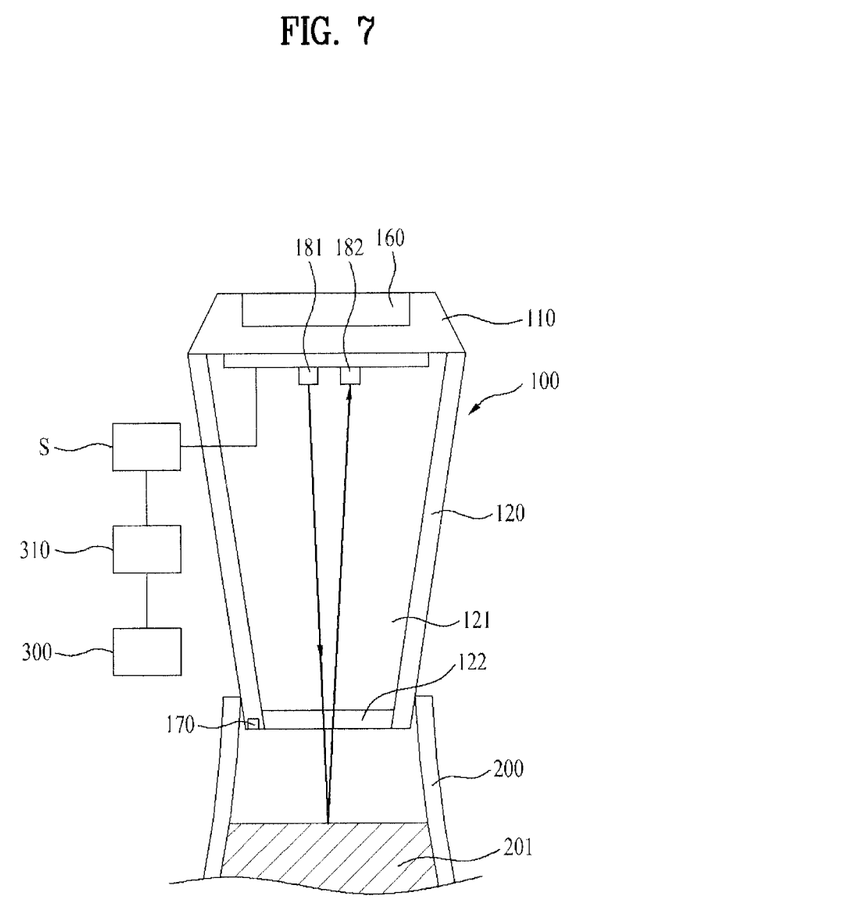
FIG. 7 is a schematic sectional view illustrating a lighting apparatus according to a fourth embodiment of the present invention.

FIG. 7 is a schematic sectional view illustrating a lighting apparatus according to a fourth embodiment of the present invention.

The lighting apparatus 100 according to the fourth embodiment of the present invention may further include the level sensing unit described with reference to FIG. 6.

The level sensing unit may include an ultrasonic wave transmitting transducer 181 to transmit ultrasonic waves and an ultrasonic wave receiving transducer 182 to receive the ultrasonic waves reflected from a surface of contents received in the storage container.

Specifically, the ultrasonic wave transmitting transducer 181 and the ultrasonic wave receiving transducer 182 are installed to the second body 110. The ultrasonic wave transmitting transducer 181 transmits ultrasonic waves along the light guide hole 121 such that the ultrasonic waves reach the surface of contents received in the storage container through the transparent window 122. Then, as the ultrasonic wave receiving transducer 182 receives the ultrasonic waves reflected from the surface of the contents, the level of the contents received in the storage container can be sensed.

Figure 9:
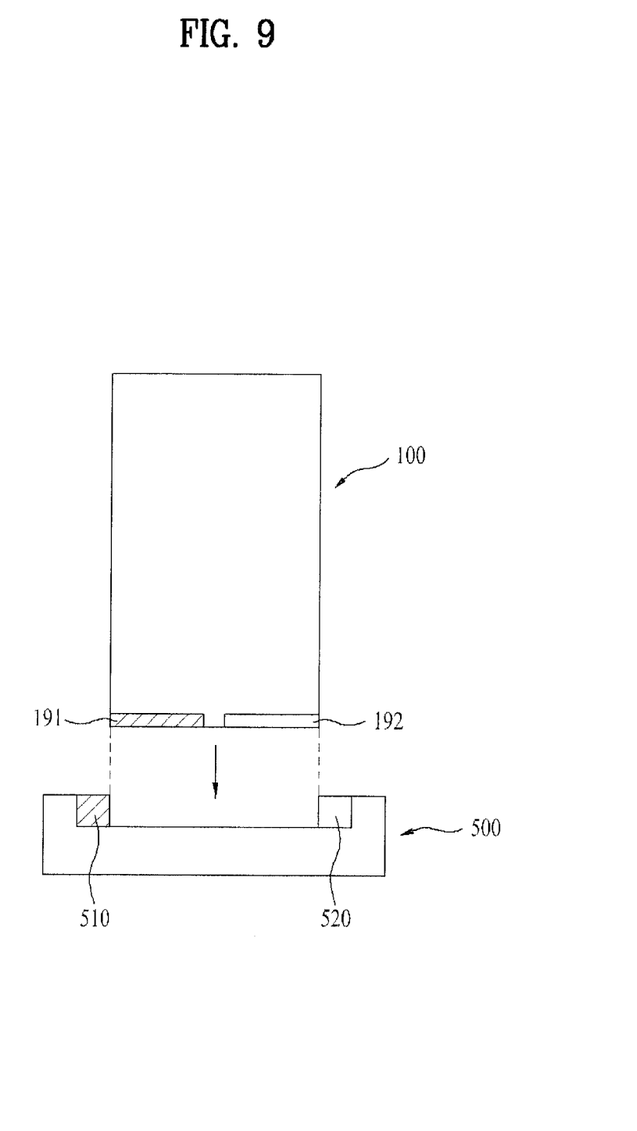
FIG. 9 is a schematic sectional view illustrating a charging device for a lighting apparatus according to the present invention.

FIG. 9 is a schematic sectional view illustrating a charging device for the lighting apparatus according to the present invention.

The lighting apparatus 100 of the present invention may include a charging device and a battery for charging of power.

The lighting apparatus 100 (or a cover member) of the present invention may be provided at an outer circumferential surface thereof with first and second terminals 191 and 192 spaced apart from each other for charging.

The first and second terminals 191 and 192 are preferably provided at an outer circumferential surface of the first body of the lighting apparatus 100.

In addition, a separate charging device 500 may be provided to charge the lighting apparatus 100 according to the present invention. The charging device 500 may have a recess, and third and fourth terminals 510 and 520 may be provided at an inner surface of the recess so as to come into contact with the first and second terminals 191 and 192 respectively.

With this configuration, if the lighting apparatus 100 or a cover member according to the present invention is inserted into the recess of the charging device 500, the first and second terminals 191 and 192 are brought into contact with the third and fourth terminals 510 and 520, thereby supplying power to the lighting apparatus 100.

In this case, the first terminal 191 and the third terminal 510 may be positive terminals, and the second terminal 192 and the fourth terminal 520 may be negative terminals.

Of course, the polarity of the respective terminals may be changed reverse.

Figure 10:
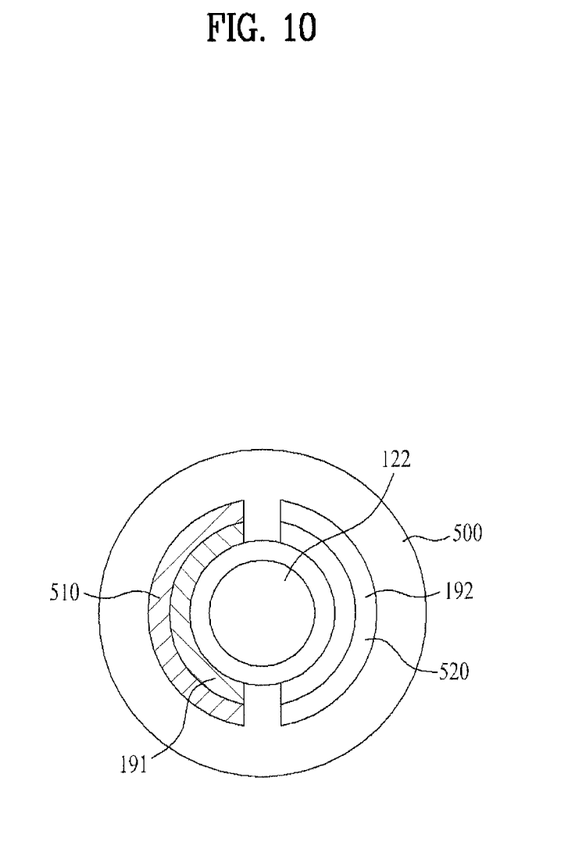
FIG. 10 is a schematic sectional view illustrating a state in which the charging device is inserted into the lighting apparatus according to the present invention.

Referring to FIG. 10, in a state in which the lighting apparatus 100 or a cover member is inserted into the recess of the charging device 500, the first terminal 191 comes into contact with the third terminal 510 and the second terminal 192 comes into contact with the fourth terminal 520.

In summary, the lighting apparatus according to the present invention may include the charging terminals provided at the outer circumferential surface thereof and the separate charging device may include the corresponding terminals provided at the inner surface of the recess indented therein, whereby the lighting apparatus can be simply charged by being seated on the charging device.

As is apparent from the above description, a lighting apparatus according to the embodiments of the present invention has the effect of achieving improved aesthetics by irradiating mood lighting into a storage container and also, of functioning to display a variety of status information about the storage container to the outside and to sterilize the interior of the storage container.

It will be apparent to those skilled in the art that various modifications and variations can be made in the present invention without departing from the spirit or scope of the invention. Thus, it is intended that the present invention covers the modifications and variations of this invention provided they come within the scope of the appended claims and their equivalents.

What is claimed is:

1. A lighting apparatus, comprising:
   a storage container having an opening; and
   a cover member including a main body to selectively open or close the opening of the storage container, a light-emitting device provided in the main body to irradiate light into the storage container, an electronic module to apply power to the light-emitting device, a switch to connect the light-emitting device and the electronic module to each other, and a controller to control operation of the light-emitting device,
   wherein the main body includes
   a first body having a channel provided longitudinally through the first body such that both longitudinal ends are open,
   a second body provided at a first longitudinal end of the first body and housing the light-emitting device, and
   a transparent window provided inside the channel in the first body, and
   wherein the light-emitting device is configured to direct light from the second body through the channel, the transparent window and the second longitudinal end of the first body,
   wherein the controller includes a display provided at the second body to display status information,
   wherein the status information includes a temperature of contents in the storage container,
   wherein the cover member further includes a temperature sensor,
   wherein the controller includes an input interface to input a control command including an operating mode,
   wherein the operating mode includes a sterilization mode and a mood lighting mode, and
   wherein the light emitting device includes an Ultra Violet-C (UVC) light-emitting diode to irradiate UVC light and an ornamental light-emitting diode to irradiate mood lighting.

2. The lighting apparatus according to claim 1, wherein:
   the status information includes information to sterilize an interior of the storage container.

3. The lighting apparatus according to claim 1, wherein:
   the status information includes a level of contents in the storage container; and
   the cover member further includes an ultrasonic transducer to sense a level of the contents.

4. The lighting apparatus according to claim 1, wherein:
   the display includes a touch screen; and
   the input interface is provided on the touch screen.

5. The lighting apparatus according to claim 1, wherein the first body is made of rubber or an elastic resin so as to be inserted into a bottle or a container.

6. The lighting apparatus according to claim 1, further including
   a first and a second terminal provided at an outer circumferential surface of the first body, and
   a charging device configured to be removably seated on the first body to charge the electronic module and having third and fourth terminals corresponding to the first and second terminals.

7. The lighting apparatus of claim 1, wherein the display is provided on an upper surface of the second body opposite the first body.

8. The lighting apparatus of claim 1, wherein the temperature sensor is provided on a distal end of the first body toward a liquid stored in the storage container.

9. A lighting apparatus, comprising:
   a cover member having a body to selectively open or close an opening of a storage container;
   a light-emitting device provided in a main body to direct light into the storage container, the light-emitting device including a substrate and at least one light emitting diode (LED) provided on the substrate;
   an electronic module to apply power to the light-emitting device;
   a switch to connect the light-emitting device and the electronic module to each other; and
   a controller to control operation of the light-emitting device,
   wherein a cavity is formed in the body to extend from an opening at a bottom surface of the main body and the substrate is provided near a distal end of the cavity such that the at least one LED directs light though the cavity toward the opening at the bottom surface,
   wherein the controller includes a display provided at a second body to display status information,
   wherein the status information includes a temperature of contents in the storage container,
   wherein the cover member further includes a temperature sensor,
   wherein the controller includes an input interface to input a control command including an operating mode,
   wherein the operating mode includes a sterilization mode and a mood lighting mode and
   wherein the light emitting device includes an Ultra Violet-C (UVC) light-emitting diode to irradiate UVC light and an ornamental light-emitting diode to irradiate mood lighting.

10. The lighting apparatus according to claim 9, wherein a transparent window is provided at the opening of the bottom surface, and the light-emitting device is configured to direct light into the storage container through the transparent window.

11. The lighting apparatus according to claim 9, wherein the body has a conical shape having a diameter at an upper portion greater than a diameter at the bottom surface of the body.

12. The lighting apparatus according to claim 9, wherein at least a portion of the body is made of rubber or an elastic resin so as to be inserted into a bottle or a container.

13. The lighting apparatus according to claim 9, wherein the ornamental light-emitting diode is a package containing at least one of a red light-emitting diode chip, a green light-emitting diode chip or a blue light-emitting diode, and is mounted on a substrate.

14. The lighting apparatus according to claim 9, further comprising an ultrasonic transducer to sense a level of contents inside the bottle or the container.

15. The lighting apparatus according to claim 9, wherein:
a first set of electrical terminals are provided at an outer circumferential surface of the body; and
the lighting apparatus includes a charging device separably seated on the body to charge the electronic module and having a second set of electrical terminals corresponding to the first set of terminals.

16. A lighting apparatus, comprising:
a storage container having an opening; and
a cover member including a main body to selectively open or close the opening of the storage container, a light-emitting device provided in the main body to irradiate light into the storage container, an electronic module to apply power to the light-emitting device, a switch to connect the light-emitting device and the electronic module to each other, and a controller to control operation of the light-emitting device,
wherein the main body includes
a first body having a channel provided longitudinally through the first body such that both longitudinal ends are open,
a second body provided at a first longitudinal end of the first body and housing the light-emitting device, and
a transparent window provided inside the channel in the first body,
wherein the light-emitting device is configured to direct light from the second body through the channel, the transparent window and the second longitudinal end of the first body,
wherein the controller includes a display provided at the second body to display status information,
wherein the status information includes a temperature of contents in the storage container,
wherein the cover member further includes a temperature sensor,
wherein the controller includes an input interface to input a control command including an operating mode,
wherein the operating mode includes a sterilization mode and a mood lighting mode,
wherein the light emitting device includes an Ultra Violet-C (UVC) light-emitting diode to irradiate UVC light and an ornamental light-emitting diode to irradiate mood lighting, and
wherein the temperature sensor is provided on a distal end of the first body toward a liquid stored in the storage container and the temperature sensor is positioned outside the channel of the first body.

* * * * *